United States Patent
Zhu et al.

(10) Patent No.: US 6,772,008 B2
(45) Date of Patent: Aug. 3, 2004

(54) METHOD AND APPARATUS FOR AVOIDANCE OF PHRENIC NERVE STIMULATION DURING CARDIAC PACING

(75) Inventors: Qingsheng Zhu, Little Canada, MN (US); Julio C. Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 236 days.

(21) Appl. No.: 09/966,818

(22) Filed: Sep. 28, 2001

(65) Prior Publication Data

US 2003/0065365 A1 Apr. 3, 2003

(51) Int. Cl.⁷ .............................................. A61N 1/365
(52) U.S. Cl. ........................... 607/9; 607/20; 600/595; 600/484
(58) Field of Search ................................ 607/9, 17, 19, 607/20, 18, 28; 600/513, 484, 587, 595, 483

(56) References Cited

U.S. PATENT DOCUMENTS

| | | | |
|---|---|---|---|
| 3,903,897 A | 9/1975 | John et al. .................. 128/419 |
| 4,114,627 A | 9/1978 | Lewyn et al. .......... 128/419 PT |
| 4,892,102 A | 1/1990 | Astrinsky ................... 128/642 |
| 5,172,694 A | 12/1992 | Flammang et al. ......... 128/642 |
| 5,222,493 A | 6/1993 | Sholder ................... 128/419 P |
| 5,265,604 A | 11/1993 | Vince ........................... 607/42 |
| 5,324,310 A | 6/1994 | Greeninger et al. .......... 607/28 |
| 5,331,966 A | 7/1994 | Bennett et al. ............. 128/696 |
| 5,431,693 A | 7/1995 | Schroeppel ................... 607/28 |
| 5,443,485 A | 8/1995 | Housworth et al. .......... 607/28 |
| 5,571,144 A | 11/1996 | Schroeppel ................... 607/28 |
| 5,601,615 A | 2/1997 | Markowitz et al. .......... 607/28 |
| 5,649,968 A * | 7/1997 | Alt et al. ...................... 607/19 |
| 5,718,720 A | 2/1998 | Prutchi et al. ................ 607/28 |
| 5,766,225 A | 6/1998 | Kramm ......................... 607/4 |
| 5,843,136 A | 12/1998 | Zhu et al. ..................... 607/13 |
| 5,861,012 A | 1/1999 | Stroebel ...................... 607/28 |
| 5,873,898 A | 2/1999 | Hemming et al. ............ 607/28 |
| 6,058,328 A | 5/2000 | Levine et al. ................. 607/14 |
| 6,128,535 A | 10/2000 | Maarse ........................ 607/28 |
| 6,230,061 B1 | 5/2001 | Hartung ..................... 607/122 |
| 6,266,564 B1 | 7/2001 | Hill et al. ...................... 607/9 |
| 6,493,586 B1 * | 12/2002 | Stahmann et al. ............ 607/27 |

* cited by examiner

Primary Examiner—Kennedy Schaetzle
(74) Attorney, Agent, or Firm—Schwegman, Lundberg, Woessner & Kluth, P.A.

(57) ABSTRACT

A cardiac rhythm management device in which an accelerometer is used to detect diaphragmatic or other skeletal muscle contraction associated with the output of a pacing pulse. Upon detection of diaphragmatic contraction, the device may be configured to automatically adjust the pacing pulse energy and/or pacing configuration.

22 Claims, 3 Drawing Sheets

METHOD AND APPARATUS FOR AVOIDANCE OF PHRENIC NERVE STIMULATION DURING CARDIAC PACING

FIELD OF THE INVENTION

This invention pertains to methods and apparatus for cardiac rhythm management. In particular, the invention relates to methods and apparatus for cardiac pacing with electrical stimulation.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate.

Pacemakers are usually implanted subcutaneously or submuscularly on a patient's chest and have leads threaded intravenously into the heart to connect the device to electrodes used for sensing and pacing. Leads may also be positioned on the epicardium by various means. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber via the same or different electrode used for sensing the chamber.

Electrical stimulation of the heart through the internal electrodes, however, can also cause unwanted stimulation of skeletal muscle. The left phrenic nerve, which provides innervation for the diaphragm, arises from the cervical spine and descends to the diaphragm through the mediastinum where the heart is situated. As it passes the heart, the left phrenic nerve courses along the pericardium, superficial to the left atrium and left ventricle. Because of its proximity to the electrodes used for pacing, the nerve can be stimulated by a pacing pulse. The resulting involuntary contraction of the diaphragm can be quite annoying to the patient, similar to a hiccup.

SUMMARY OF THE INVENTION

The present invention is a cardiac rhythm management device that is configured to detect when unwanted stimulation of skeletal muscle such as the diaphragm occurs during pacing by sensing the resulting acceleration imparted to the device housing. Signal processing techniques may be used to distinguish the acceleration that results from skeletal muscle contraction from that due to cardiac contraction (i.e., heart sounds). If skeletal muscle contraction occurs, the device may then decrease the pacing pulse energy. When adjusting the pacing pulse energy, a capture verification test may be performed by sensing evoked potentials during pacing in order to ensure that pacing pulses have adequate energy to stimulate the heart. In another embodiment, the pacing configuration used for outputting pacing pulses may be modified to result in a pacing vector less likely to cause skeletal muscle contraction.

DETAILED DESCRIPTION

The present invention is applicable to all types of cardiac rhythm management devices that have a pacing functionality including bradycardia pacing, anti-tachycardia pacing, and cardiac resynchronization pacing. After a description of the basic hardware components and operating modes of a pacemaker, exemplary embodiments of the invention will be set forth.

1. Device Description

Figure 1:
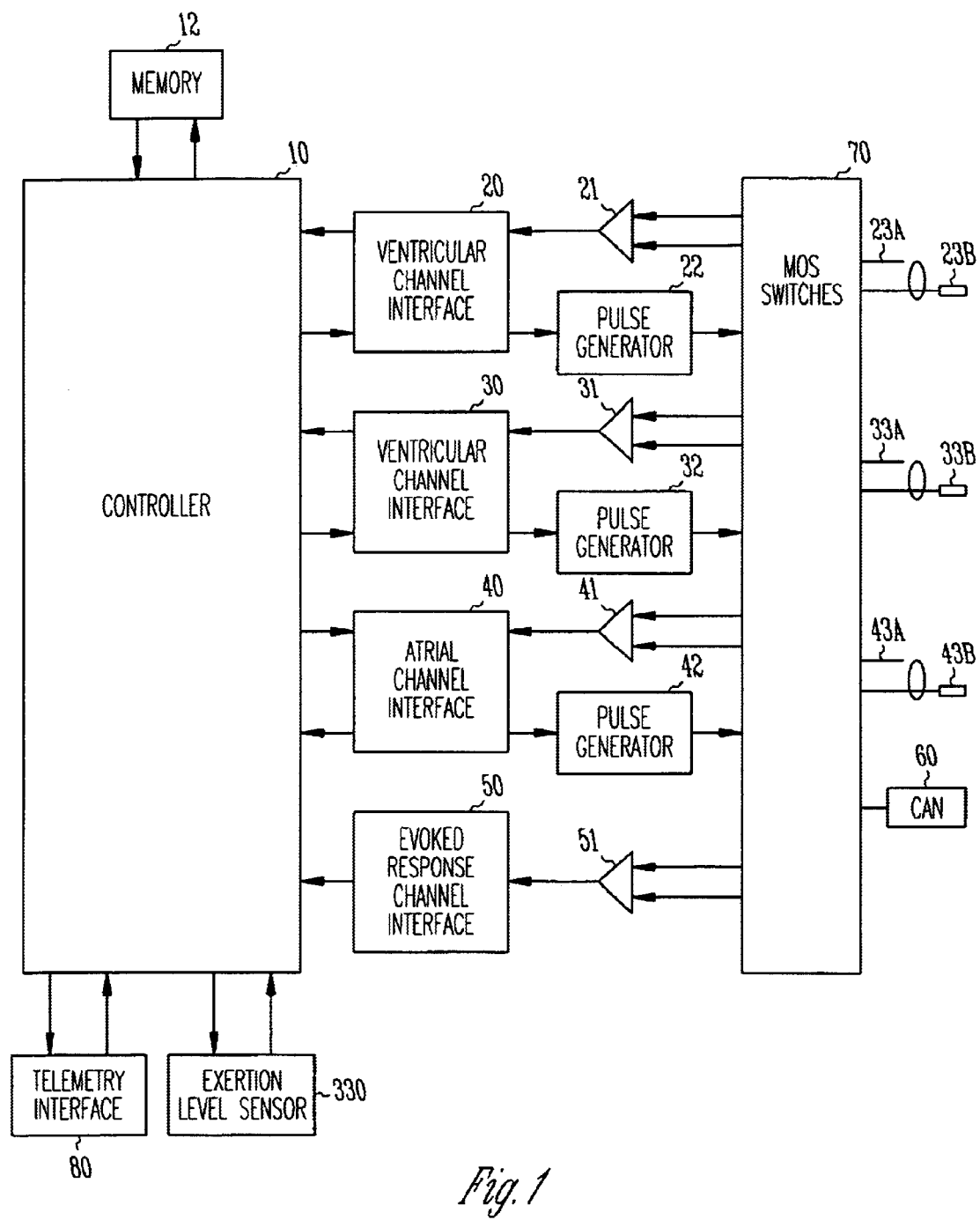
FIG. 1 is a system diagram of a cardiac rhythm management device configured for evoked potential sensing.

A block diagram of a multi-site pacemaker having an atrial and two ventricular pacing channels is shown in FIG. 1. The control unit of the pacemaker is made up of a microprocessor 10 communicating with a memory 12 via a bidirectional data bus, where the memory 12 typically comprises a ROM (read-only memory) for program storage and a RAM (random-access memory) for data storage. The control unit could be implemented by other types of logic circuitry (e.g., discrete components or programmable logic arrays) using a state machine type of design, but a microprocessor-based system is preferable. The control unit is capable of operating the pacemaker in a number of programmed modes where a programmed mode defines how pacing pulses are output in response to sensed events and expiration of time intervals. Bradycardia pacing modes refer to pacing algorithms used to pace the atria and/or ventricles when the intrinsic atrial and/or ventricular rate is inadequate due to, for example, AV conduction blocks or sinus node dysfunction. Such modes may either be single-chamber pacing, where either an atrium or a ventricle is paced, or dual-chamber pacing in which both an atrium and a ventricle are paced. Another type of pacing is anti-tachycardia pacing where the heart is paced competitively in order to slow an abnormally fast rhythm. Pacemakers can also be employed to improve the coordination of cardiac contractions by timed pacing of selected chambers or sites, termed cardiac resynchronization therapy. Additional sensing of physiological data allows the pacemaker to change the rate at which it paces the heart in accordance with some parameter correlated to metabolic demand, referred to as rate-adaptive pacing. One such parameter is the activity level of the patient. In the device of FIG. 1, an accelerometer 330 senses accelerations imparted to the device housing brought about by changes in the patient's physical activity. A telemetry interface 80 is also provided for communicating with an external programmer.

The pacemaker has an atrial sensing/pacing channel comprising ring electrode 43a, tip electrode 43b, sense amplifier 41, pulse generator 42, and an atrial channel interface 40 which communicates bidirectionally with a port of microprocessor 10. The device also has two ventricular sensing/pacing channels that include ring electrodes 23a and 33b, tip electrodes 23b and 33b, sense amplifiers 21 and 31, pulse generators 22 and 32, and ventricular channel interfaces 20 and 30. The electrodes are electrically connected to the device by means of a lead. The ring and tip electrode associated with each channel can be used for bipolar sensing or pacing or, as described below, different electrodes can be connected to each channel through a switching circuit 70 to result in different unipolar sensing or pacing vectors. The sensing circuitry of the pacemaker generates atrial and ventricular sense signals when voltages sensed by the electrodes exceed a specified threshold. The pacemaker also has an evoked response sensing channel that comprises an evoked response channel interface 50 and a sense amplifier 51. The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or changing the pacing pulse amplitude.

The controller 10 controls the overall operation of the device in accordance with programmed instructions stored in memory. The controller 10 interprets sense signals from the sensing channels and controls the delivery of paces in accordance with a pacing mode. The controller is also interfaced to a switching circuit 70 through which the electrodes are connected to the sense amplifiers and pulse generators. The controller is thus able to connect the amplifiers and/or pulse generators to selected tip or ring electrodes of any of the sensing/pacing channels that connect through the switching circuit 70. Each sense amplifier amplifies the voltage difference between two inputs, and the inputs may be selected from any of the tip or ring electrodes or the pacemaker case or can 60, which is also electrically connected to the switching circuit. The device has the capability of connecting a pulse generator such that a pacing voltage pulse appears across any of the tip or ring electrodes or across an electrode and the can 60. A particular set of electrodes and one or more pulse generators used to output pacing pulses is referred to herein as a pacing configuration.

Figure 2:
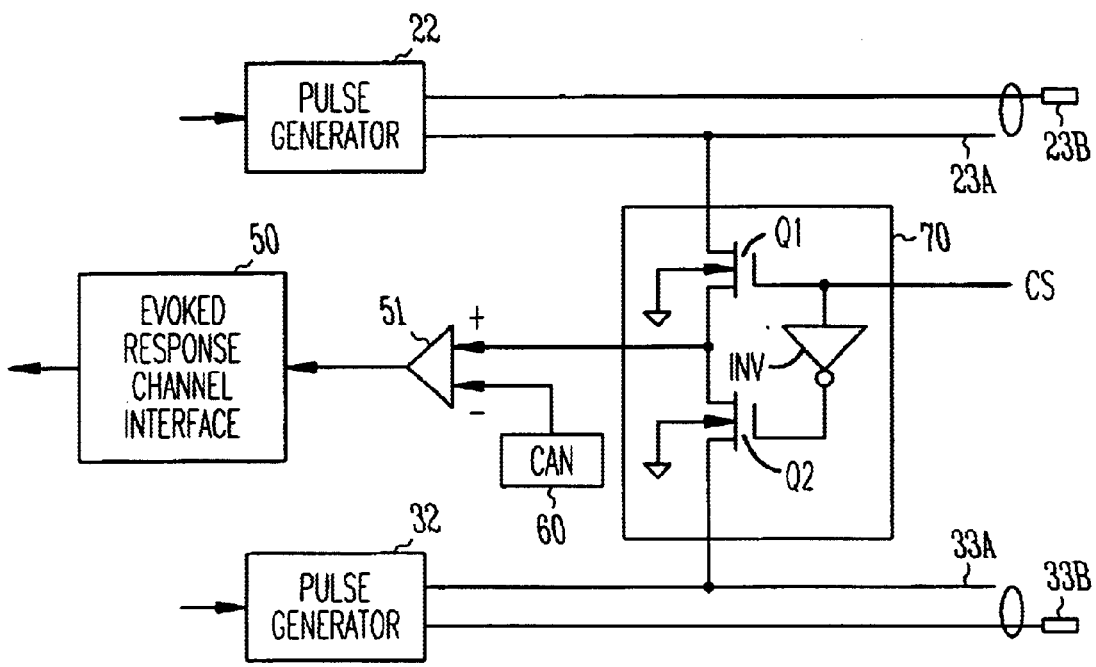
FIG. 2 illustrates an exemplary switching circuit.

The switching circuit 70 may be implemented as an array of MOSFET transistors controlled by outputs of the controller 10. FIG. 2 shows a portion of a basic exemplary switching circuit. In this circuit, a pair of MOSFET transistors Q1 and Q2 along with inverter INV form a double-pole switch that switches one of the inputs to amplifier 51 between ring electrode 23a and 33a in accordance with a control signal CS from the controller. The other input is shown as being connected to can 60, but in other embodiments it may also be switched to one of the electrodes by means of the switching circuit. In a more complicated version of the same basic pattern, the switching circuit 70 may be able to switch the amplifier inputs or pulse generator outputs to any of the tip or ring electrodes of the sensing/pacing channels or to the can 60.

2. Capture Verification

In order for a pacemaker to control the heart rate in the manner described above, the paces delivered by the device must achieve "capture," which refers to causing sufficient depolarization of the myocardium that a propagating wave of excitation and contraction result (i.e., a heart beat). A pacing pulse that does not capture the heart is thus an ineffective pulse. This not only wastes energy from the limited energy resources (battery) of pacemaker, but can have deleterious physiological effects as well, since a demand pacemaker that is not achieving capture is not performing its function in enforcing a minimum heart rate. A number of factors can determine whether a given pacing pulse will achieve capture including the energy of the pulse, which is a function of the pulse's amplitude and duration or width, and the integrity and physical disposition of the pacing lead.

A common technique used to determine if capture is present during a given cardiac cycle is to look for an "evoked response" immediately following a pacing pulse. The evoked response is the wave of depolarization that results from the pacing pulse and evidences that the paced chamber has responded appropriately and contracted. By detecting the evoked P-wave or evoked R-wave, the pacemaker is able to detect whether the pacing pulse (A-pulse or V-pulse) was effective in capturing the heart, that is, causing a contraction in the respective heart chamber. In order for a pacemaker to detect whether an evoked P-wave or an evoked R-wave occurs immediately following an A-pulse or a V-pulse, a period of time, referred to as the atrial capture detection window or the ventricular capture detection window, respectively, starts after the generation of the pulse. Sensing channels are normally rendered refractory (i.e., insensitive) for a specified time period immediately following a pace in order to prevent the pacemaker from mistaking a pacing pulse or afterpotential for an intrinsic beat. This is done by the pacemaker controller ignoring sensed events during the refractory intervals, which are defined for both atrial and ventricular sensing channels and with respect to both atrial and ventricular pacing events. Furthermore, a separate period that overlaps the early part of a refractory interval is also defined, called a blanking interval during which the sense amplifiers are blocked from receiving input in order to prevent their saturation during a pacing pulse. If the same sensing channels are used for both sensing intrinsic activity and evoked responses, the capture detection window must therefore be defined as a period that supercedes the normal refractory period so that the sensing circuitry within the pacemaker becomes sensitive to an evoked P-wave or R-wave.

Capture verification can be performed by delivering a pacing pulse and attempting to sense an evoked response using either the same or different electrodes used for pacing. In an exemplary embodiment shown in FIG. 1, a capture verification test is performed using a dedicated evoked response sensing channel that includes a sense amplifier for sensing an evoked response generated after a pacing pulse is delivered. The amplifier input of the evoked response sensing channel is switched via switching circuit 70 to selected electrodes of the sensing/pacing channels before the capture verification test is performed. After switching the input of the evoked response sensing channel to the selected electrodes, a pacing pulse is output and an evoked response is either detected or not, signifying the presence or loss of capture, respectively. Although the same electrodes can be used for pacing and evoked response detection during a capture verification test, the input of the evoked response sensing channel preferably is switched to electrodes of another sensing/pacing channel. The particular electrodes used for evoked response detection can be selected in accordance with which electrodes produce a sensing vector that most easily senses an evoked response due to the pacing electrodes. The sense amplifier of the evoked response sensing channel is then blanked during the capture verification test for a specified blanking period following a pacing pulse output by the tested sensing/pacing channel. The blanking period is followed by a capture detection window during which an evoked response may be sensed by the evoked response sensing channel. In an exemplary embodiment, the blanking period may be approximately 10 ms, and the width of the capture detection window may range from 50 to 350 ms.

3. Detection and Avoidance of Skeletal Muscle Stimulation

As noted above, pacing pulses can stimulate the phrenic nerve and cause contraction of the diaphragm. It is also possible for unipolar pacing configurations to produce a pacing vector that stimulates the pectoral muscles overlying the internal electrodes, resulting in so-called pocket twitch. Both types of skeletal muscle stimulation can be very annoying to a patient. Abrupt contractions of either the pectoral muscles or the diaphragm will impart an acceleration to the implanted housing of the pacemaker. In order to detect whether pacing pulses are producing such unwanted muscle contractions, the controller 10 can be configured to use the accelerometer 330 to sense any accelerations experienced by the device housing that coincide with the output of a pacing pulse. Contraction of the heart and the resulting heart sounds, however, can also impart an acceleration to the device housing that coincides with a pacing pulse. In order to distinguish this type of acceleration from that due to skeletal muscle contraction, signal processing techniques can be used. For example, the acceleration signal produced by the accelerometer 330 during an intrinsic heartbeat or a low-energy paced heartbeat with no accompanying skeletal muscle contraction can be recorded and processed to produce a cardiac signature in either the time or frequency domain that can be compared with accelerometer signals obtained while pacing. An accelerometer signal obtained during a pacing time window starting with a pacing pulse (e.g. 10 to 100 milliseconds post-pace) that contains frequency components different from that of the cardiac signature or is uncorrelated with the cardiac signature in the time domain, for example, can be assumed to be due to skeletal muscle contraction. In an alternative embodiment, the patient may undergo clinical testing in which diaphragmatic contractions or pocket twitches are intentionally produced by varying the pacing energy and/or pacing configuration in order to obtain a skeletal muscle contraction signature from an accelerometer measurement during the pacing time window. The skeletal muscle signature can then be compared in either the time or frequency domain with accelerometer measurements taken within the pacing time window to determine if the acceleration is due to skeletal muscle contraction.

Figure 3:
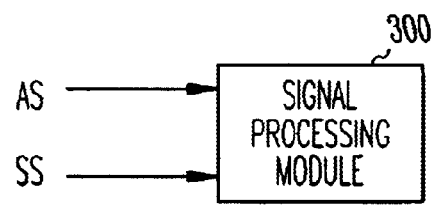
FIG. 3 illustrates an exemplary signal processing module.

FIG. 3 illustrates a signal processing module 300 for performing the comparison between an accelerometer signal and a signature as described above. The module 300 may be incorporated into the controller either as code executed by the microprocessor or as one or more discrete hardware components and compares the accelerometer signal AS obtained during the pacing time window with a signature signal SS. As noted above, such a comparison may be performed in either the time domain or the frequency domain. In a particular embodiment, the module 300 may be a matched finite impulse response filter that performs a cross-correlation between the accelerometer signal AS and the recorded signature signal SS. The recorded signature signal SS is represented in that case by the filter coefficients of the matched filter (i.e., the impulse response of the filter corresponds to a time-reversed version of the signature signal SS).

Once it is determined that unwanted skeletal muscle contractions are occurring with pacing pulses, the controller may be further programmed to make adjustments in the operation of the device. In one embodiment, capture verification tests can be performed as the pacing pulse energy is reduced until a pacing pulse energy is found that both achieves capture and produces no skeletal muscle contraction. In other embodiments, the pacing configuration can be varied. For example, different pacing vectors can be tried by switching the output of a pulse generator to different electrodes with the switching circuit 70. Switching from a unipolar to a bipolar pacing configuration, for example, may prevent pacing pulses from causing pectoral muscle contraction. Other pacing configurations with different pacing vectors may be less likely to stimulate the phrenic nerve. In the case of multi-site pacing, different pacing configurations using fewer or different pacing sites may also be tried.

Figure 4:
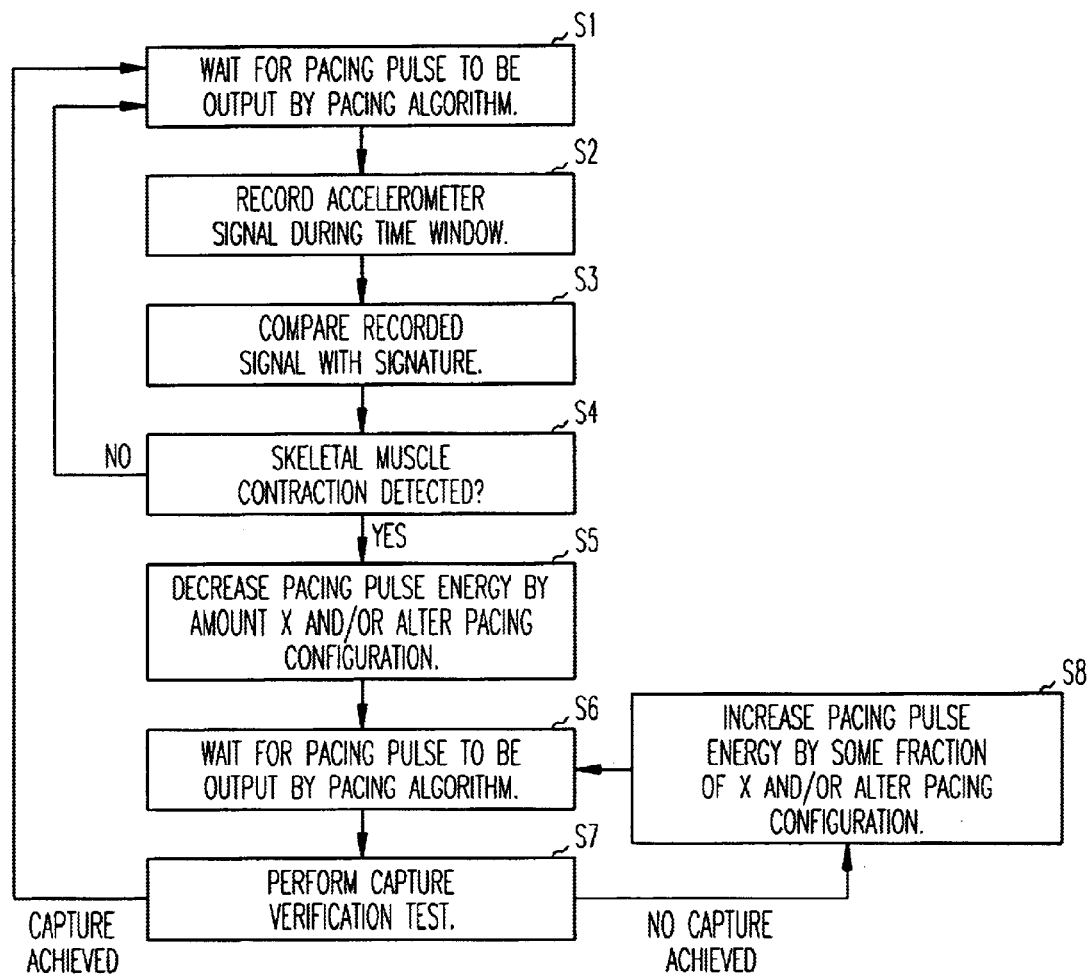
FIG. 4 is a flow diagram illustrating an exemplary method for automatically the adjusting the pulse energy and/or pacing configuration in accordance with accelerometer signals.

FIG. 4 is a diagram illustrating the steps performed by an exemplary system for automatically adjusting device operation as it could be implemented in software executed by the controller and/or with dedicated hardware components. At step S1, the system waits for the pacing algorithm to output a pacing pulse and then records the accelerometer signal during a specified pacing time window after the pace (e.g. 10 to 100 milliseconds post-pace). A time domain or frequency domain comparison is then performed between the accelerometer signal and either a cardiac or skeletal muscle signature at step S3. At step S4, a determination is made as to whether the accelerometer signal represents a skeletal muscle contraction and the system returns to step S1 if not. Otherwise, the pulse energy is decreased by an amount X and/or the pacing configuration is altered at step S5, and the system waits for another pace to be output at step S6. At step S7, a capture verification test is performed. If capture is achieved the system returns to step S1. If the pace fails to achieve capture, the pulse energy is increased by some fraction of X (and/or the pacing configuration is altered in some manner that reverses the effect the alteration performed at step S5) and the system returns to step S6. Thus, in this embodiment, no further acceleration sensing is performed by steps S1 through S4 until the pulse energy and/or pacing configuration is adequate to achieve capture.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
   one or more sensing/pacing channels, each such channel comprising an electrode for disposing near a chamber of the heart, a pulse generator for outputting pacing pulses, and a sense amplifier for detecting sense signals;
   an accelerometer for sensing accelerations imparted to a device housing and generating an accelerometer signal in accordance therewith;
   a controller for controlling the operation of pulse generators used in a selected pacing configuration in accordance with a programmed pacing mode; and,
   wherein the controller is programmed to compare the accelerometer signal obtained during a pacing time window subsequent to the output of a pacing pulse with a signature to determine if skeletal muscle contraction has occurred.

2. The device of claim 1 wherein the signature represents an acceleration signal generated after an intrinsic heartbeat.

3. The device of claim 1 wherein the signature represents an acceleration signal generated after a paced beat that produces diaphragmatic contraction.

4. The device of claim 1 wherein the signature represents an acceleration signal generated after a paced beat that produces a pocket twitch.

5. The device of claim 1 wherein the comparison between the accelerometer signal and the signature is a frequency domain comparison.

6. The device of claim 1 wherein the comparison between the accelerometer signal and the signature is a time domain correlation.

7. The device of claim 1 wherein the controller is further programmed to decrease the pacing pulse energy by a specified amount if skeletal muscle contraction has been detected.

8. The device of claim 7 wherein the controller is further programmed to perform a capture verification during a subsequent pacing pulse after the pulse energy has been decreased, the capture verification test being performed by sensing whether an evoked response occurs during a capture detection window following the output of the pacing pulse, and increase the pacing pulse energy if no capture was achieved.

9. The device of claim 7 wherein the controller is further programmed to perform a capture verification during a subsequent pacing pulse after the pulse energy has been decreased, the capture verification test being performed by sensing whether an evoked response occurs during a capture detection window following the output of the pacing pulse, and to alter the selected pacing configuration if no capture was achieved.

10. The device of claim 1 further comprising:
a switching circuit for switching the inputs of selected sensing channel amplifiers and outputs of selected pulse generators to a selected electrodes of the sensing/pacing channels; and,
wherein the controller is programmed to alter the selected pacing configuration if skeletal muscle contraction has been detected.

11. The device of claim 1 further comprising a signal processing module for comparing the accelerometer signal with the signature.

12. The device of claim 11 wherein the signal processing module performs a cross-correlation between the accelerometer signal and the signature.

13. A method for operating a cardiac rhythm management device, comprising:
sensing cardiac depolarizations via one or more sensing/pacing channels, each such channel comprising an electrode for disposing near a chamber of the heart, a pulse generator for outputting pacing pulses, and a sense amplifier for detecting sense signals;
outputting pacing pulses through selected sensing/pacing channels used in a selected pacing configuration in accordance with a programmed pacing mode;
comparing an accelerometer signal obtained during a pacing time window subsequent to the output of a pacing pulse with a signature to determine if skeletal muscle contraction has occurred.

14. The method of claim 13 wherein the signature represents an acceleration signal generated after an intrinsic heartbeat.

15. The method of claim 13 wherein the signature represents an acceleration signal generated after a paced beat that produces diaphragmatic contraction.

16. The method of claim 13 wherein the signature represents an acceleration signal generated after a paced beat that produces a pocket twitch.

17. The method of claim 13 wherein the comparison between the accelerometer signal and the signature is a frequency domain comparison.

18. The method of claim 13 wherein the comparison between the accelerometer signal and the signature is a time domain correlation.

19. The method of claim 13 further comprising decreasing the pacing pulse energy by a specified amount if skeletal muscle contraction has been detected.

20. The method of claim 19 further comprising performing a capture verification during a subsequent pacing pulse after the pulse energy has been decreased, the capture verification test being performed by sensing whether an evoked response occurs during a capture detection window following the output of the pacing pulse, and increasing the pacing pulse energy if no capture was achieved.

21. The method of claim 19 further comprising performing a capture verification during a subsequent pacing pulse after the pulse energy has been decreased, the capture verification test being performed by sensing whether an evoked response occurs during a capture detection window following the output of the pacing pulse, and altering the selected pacing configuration if no capture was achieved.

22. The method of claim 13 further comprising altering the selected pacing configuration if skeletal muscle contraction has been detected by switching the inputs of selected sensing channel amplifiers and outputs of selected pulse generators to a selected electrodes of the sensing/pacing channels.

* * * * *